(12) United States Patent
Leslie

(10) Patent No.: US 9,205,989 B1
(45) Date of Patent: Dec. 8, 2015

(54) CHAIN MOUNTED PRODUCT CAPTURING GRIPPER CONSTRUCTION

(71) Applicant: John M. Leslie, Blountville, TN (US)

(72) Inventor: John M. Leslie, Blountville, TN (US)

( * ) Notice: Subject to any disclaimer, the term of this patent is extended or adjusted under 35 U.S.C. 154(b) by 0 days.

(21) Appl. No.: 13/998,298

(22) Filed: Oct. 18, 2013

Related U.S. Application Data

(60) Provisional application No. 61/958,658, filed on Aug. 2, 2013.

(51) Int. Cl.
*B65G 17/32* (2006.01)
*A61L 2/26* (2006.01)

(52) U.S. Cl.
CPC ............ *B65G 17/323* (2013.01); *B65G 17/32* (2013.01); *A61L 2/26* (2013.01)

(58) Field of Classification Search
CPC ......... B65G 17/323; B65G 17/32; B66C 1/42
See application file for complete search history.

(56) References Cited

U.S. PATENT DOCUMENTS

| | | | | |
|---|---|---|---|---|
| 3,860,104 A * | 1/1975 | Strauss | ................. | B65G 17/20 134/127 |
| 4,055,943 A * | 11/1977 | Reichert | .............. | B65G 47/842 294/116 |
| 4,573,763 A * | 3/1986 | Thomas | .................... | E01F 9/03 359/538 |
| 5,024,318 A * | 6/1991 | Schwarze | ............ | A47B 49/008 198/465.2 |
| 5,558,200 A * | 9/1996 | Whitby | ................. | B65G 17/323 198/470.1 |
| 6,264,902 B1 * | 7/2001 | Howlett | .................... | A61L 2/26 422/292 |
| 6,379,631 B1 * | 4/2002 | Wu | ........................... | A61L 2/26 422/292 |
| 6,572,819 B1 * | 6/2003 | Wu | ........................... | A61L 2/26 206/438 |
| 2001/0002291 A1 * | 5/2001 | Buschmeier | .............. | B05C 3/10 428/34.4 |
| 2011/0036684 A1 * | 2/2011 | Bonnain | ................ | B65B 21/06 198/418.7 |
| 2011/0297508 A1 * | 12/2011 | Chaigne | ................ | B65G 17/32 198/470.1 |

* cited by examiner

*Primary Examiner* — Gene Crawford
*Assistant Examiner* — Thomas Randanzzo

(57) ABSTRACT

A bottle or can gripper structure for use on a container filling machine, the structure having a molded, one piece elastomeric rectangular base from which longitudinal rows of flexible but recoverable fingers project upwardly, wherein the fingers have radiused tops, and wherein the tops lie in a plane which is angled laterally upwardly with respect to the upper surface of the base from a leading row of fingers to a trailing row of fingers.

5 Claims, 3 Drawing Sheets

CHAIN MOUNTED PRODUCT CAPTURING GRIPPER CONSTRUCTION

This application claims priority under 35 U.S.C. 119(e)(1) based on Applicants Provisional U.S. Patent Application Ser. No. 61/958,658 filed Aug. 2, 2013 of the same title.

This invention is directed to a unique and improved product gripper for use on a product capturing or clamping conveyor chain wherein parallel chains are typically made up of roller base chain links provided with a snap-on product gripping device, usually connected to each link and comprising a metal or plastic base plate for quick attachment to the link, wherein the plate has a product gripping member of resilient material such as rubber, urethane, elastomer or the like fixed onto the top surface of the base plate. Two such chains typically run on edge and parallel to each other. The products such as liquid containers are picked up in their path by squeezing them between the opposing gripping members as the chains are made to converge. The chains are able to flex within a plane substantially containing the longitudinal axes of the grippers in order to raise or lower the product being conveyed, and then the two chains separate, thereby setting the products on a conveyor or platform at a different level. See U.S. Pat. Nos. 5,219,065, and 6,851,549, the disclosures of both hereby being incorporated herein by reference in their entireties, for the general layout of product capturing chain constructions which could be used commercially with the present gripper.

The present gripper provides enhanced gripping sensitivity and universality of use as well as improved longevity and base flexibility for ease of installation.

SUMMARY OF THE PRESENT INVENTION

A container gripper structure of molded elastomeric material for use on a container carrying conveyor, the structure being a single molded unit having a base portion with a plurality of parallel longitudinal rows of upstanding fingers of circular in cross-section configuration with radiused tops, wherein the tops of laterally spaced rows fingers all lie in a plane which is angled laterally upwardly of the upper surface of the base portion from the leading row of fingers to the trailing row of fingers.

BRIEF DESCRIPTION OF THE DRAWINGS

Referring to the drawings herein wherein exemplary dimensions are given in inches and wherein the Figures show an exemplary full scale operational gripper.

DETAILED DESCRIPTION

Figure 1:
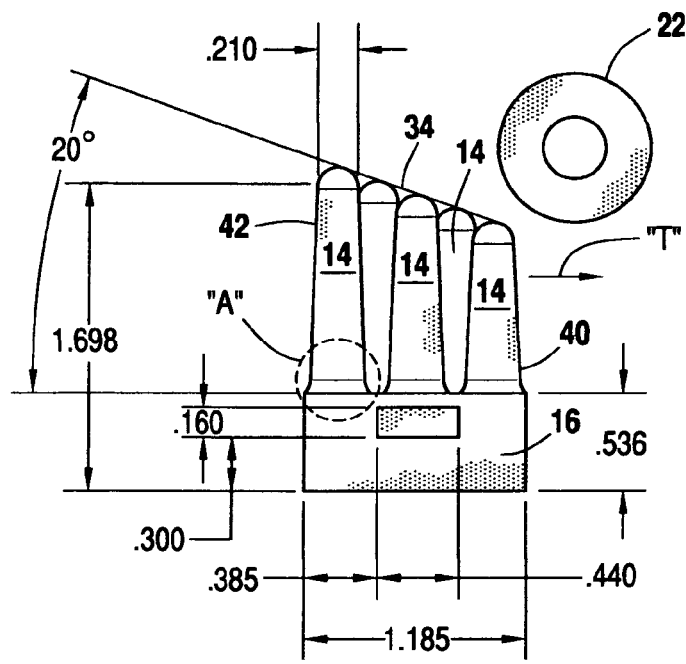
FIG. 1 is an end view of a preferred embodiment of the present elastomeric, multi-finger gripper 10 with a lower portion "A" of one exemplary finger shown in cross-section, wherein the fingers preferably are solid core, and wherein the direction of travel of the conveyor relative to a container is designated "T"
Figure 2:
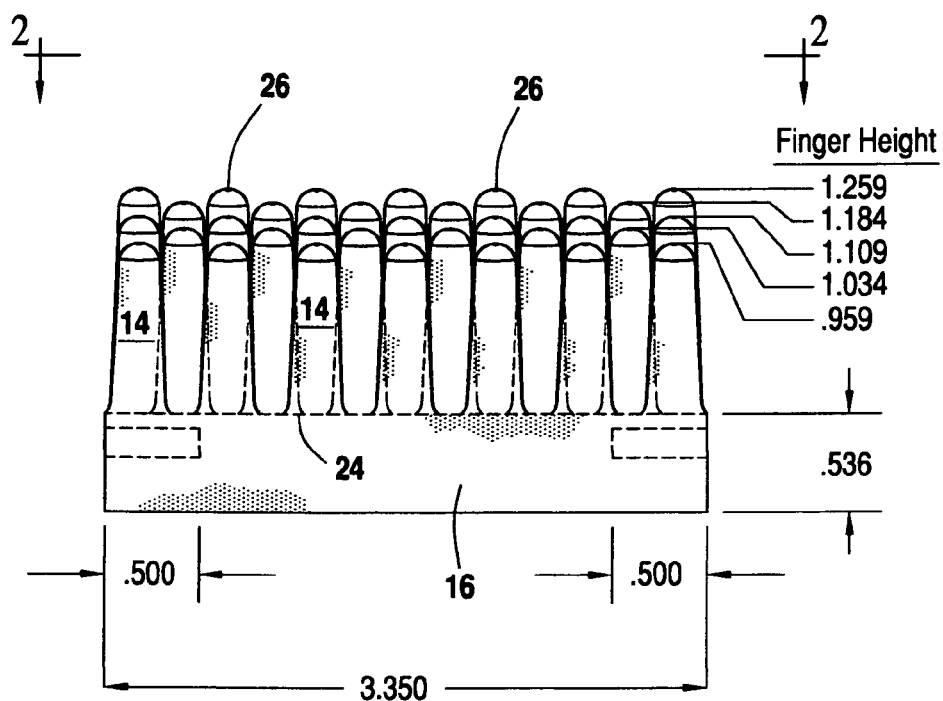
FIG. 2 is a side view of the gripper of FIG. 1.
Figure 3:
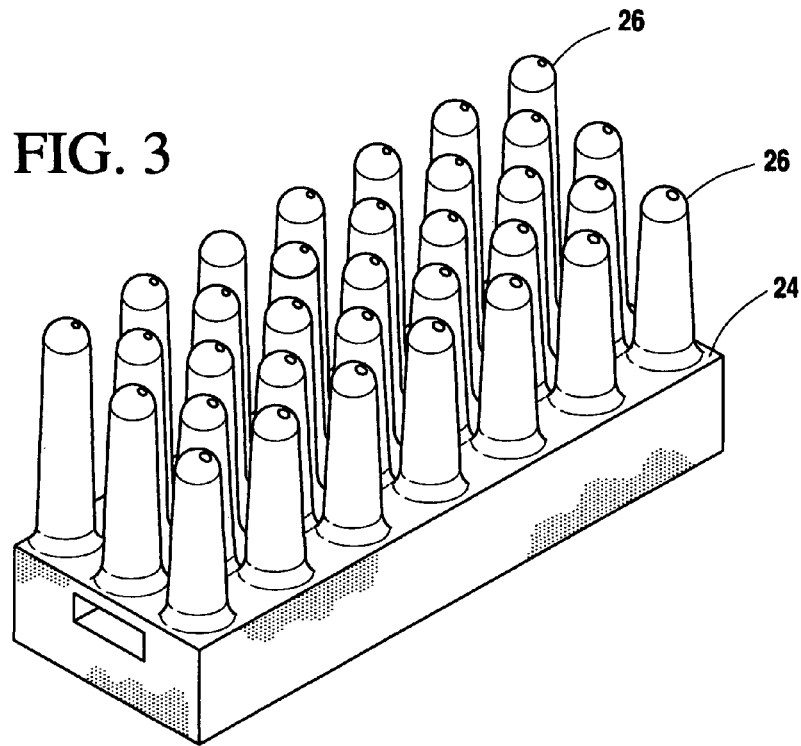
FIG. 3 is an isometric view of the gripper.
Figure 4:
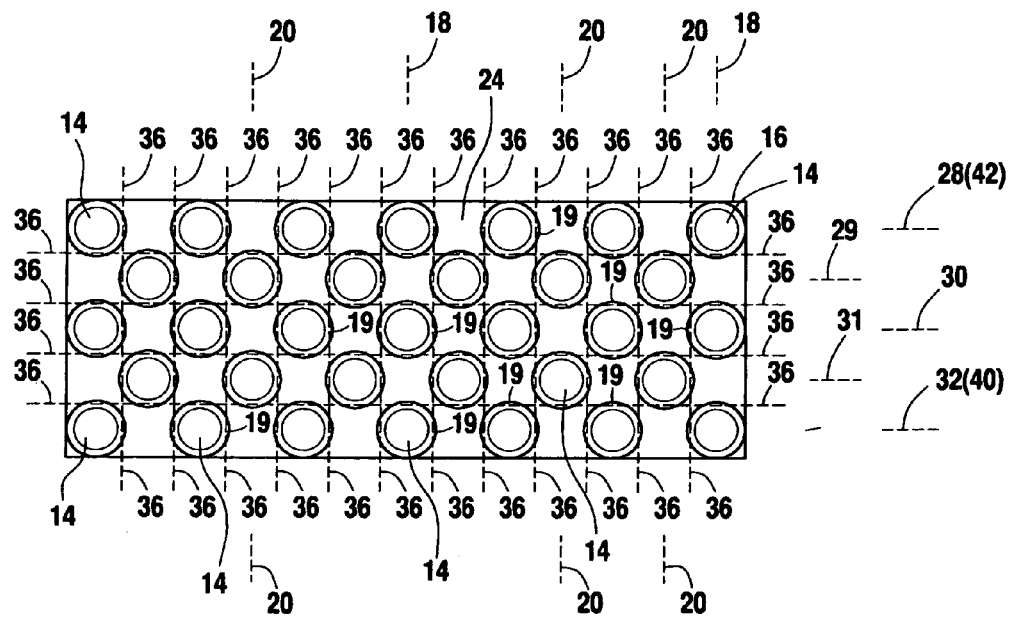
FIG. 4 is a top plan view taken along line 4-4 in FIG. 2 of the gripper showing an exemplary and preferred arrangement of the forgers 14.
Figure 5:
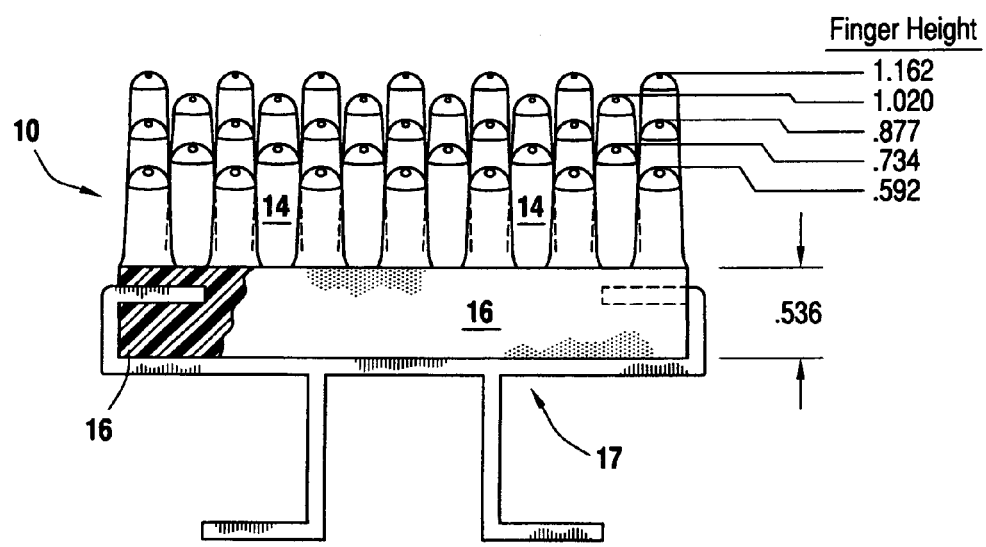
FIG. 5 is a leading edge view of the present gripper mounted on a base link 17 which is adapted for mounting on a conveyor such as shown in U.S. Pat. No. 5,219,065.
Figure 6:
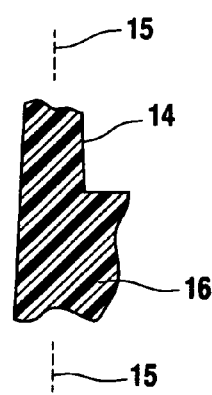
FIG. 6 is a cross-sectional view of an encircled area "A" in FIG. 2 showing a solid core version of the gripper fingers.

As shown in the drawings the gripper is constructed preferably of thermoplastic elastomeric material such as Santoprene™ 271-55 described in detail in the Exxon Mobil Chemical publication of Mar. 8, 2009, and described in general terms as "A soft, colorable specially thermoplastic vulcanizate (TPV) in the thermoplastic elastomer (TPE) family. It complies with FDA regulations for rubber articles intended for repeated use, as well as those in contact with non-fatty, non-oily foods as closures and sealing gaskets. This grade of "SANTOPRENE" TPV is shear-dependent and can be processed on conventional thermoplastics equipment for injection molding or extrusion. It is polyolefin based and completely recyclable."

The gripper fingers having a flex axes 15 are arranged preferably in longitudinally alternating lateral rows 18 and 20, the exact number of such rows depending on the particular application for which the gripper is intended. The circular in cross-section fingers are tapered inwardly slightly from bottom to top and the tops of the fingers are upwardly radiused. The laterally inner edge portions 19 of the fingers lie in a plane 36 which is perpendicular to the upper surface of the base portion 16 and slightly overlap each other.

The hardness (durometer), flexibility, resiliency, wear resistance, and the like of the gripper material can, of course, be tailored to meet the needs of the particular application such as, for example, whether the containers are filled, heavy glass bottles or lightweight aluminum empty containers.

The invention, in one preferred embodiment may be summarized further as a gripper 10 for use on a conveyor system for engaging and transporting containers 22, wherein the gripper comprises a unitary elastomeric base portion 16 having a substantially planar upper surface 24, a plurality of round in cross section elastomeric fingers 14 extending upwardly from and perpendicular to said surface 24, each said finger being tapered inwardly from bottom to top, wherein the tops 26 of said fingers are upwardly radiused, wherein a first set of said fingers are arranged in longitudinal rows 28, 30, 32, and a second set of said fingers are arranged in longitudinal rows 29, 31, wherein the lateral axes 18 of said first set are offset from the lateral axes 20 of said second set, and wherein the tops 26 of said fingers lie in a plane 34 which tapers upwardly from the leading edge 40 of said gripper to the trailing edge 42 thereof at an angle of from about 15° to about 25° to the upper surface 24 of the gripper.

The invention has been described in detail with particular reference to preferred embodiments thereof, but it will be understood that variations and modifications will be effected within the spirit and scope of the invention.

I claim:

1. A container gripper for use on a conveyor system for engaging and transporting containers, wherein the gripper comprises a unitary elastomeric base portion having a longitudinal dimension and a lateral dimension and a substantially planar upper surface, a plurality of round in cross section elastomeric fingers extend upwardly from and perpendicular to said surface and are laterally and longitudinally spaced from each other, each said finger being individually formed around a flex axis of the finger and being tapered inwardly from bottom to top, wherein the tops of said fingers are upwardly radiused, wherein a first set of said fingers are arranged in longitudinal and lateral rows, and a second set of said fingers are arranged in longitudinal and lateral rows, wherein said first and second row sets are parallel and alternately laterally and longitudinally arranged and spaced apart, and wherein the tops of all said fingers lie in a plane which tapers upwardly from a leading row of said fingers to a trailing row of said fingers at a lateral contact angle.

2. The gripper of claim 1 wherein said contact angle is from about 15° to about 25° to said upper surface of the gripper.

3. The gripper of claim 2 wherein laterally inner edge portions of the fingers which are in longitudinal rows of adjacent first and second row sets lie in a common plane which is perpendicular to said upper surface of said base portion and slightly overlap each other.

4. The gripper of claim 3 wherein said first set of fingers comprises three longitudinal rows and seven lateral rows, and wherein said second set of fingers comprises two longitudinal rows and six lateral rows.

5. The gripper of claim 4 wherein said base portion and said fingers are solid elastomeric material and integrally molded.

* * * * *